United States Patent
Duneas

(10) Patent No.: US 7,728,116 B2
(45) Date of Patent: Jun. 1, 2010

(54) METHOD OF PREPARING AN OSTEOGENIC PROTEIN FRACTION

(75) Inventor: Nicolaas Duneas, Boksburg North (ZA)

(73) Assignee: Altis Biologics (Proprietary) Limited, Groenkloof (ZA)

( * ) Notice: Subject to any disclaimer, the term of this patent is extended or adjusted under 35 U.S.C. 154(b) by 812 days.

(21) Appl. No.: 10/518,723

(22) PCT Filed: Jun. 18, 2003

(86) PCT No.: PCT/IB03/02354

§ 371 (c)(1), (2), (4) Date: Aug. 10, 2005

(87) PCT Pub. No.: WO2004/004630

PCT Pub. Date: Jan. 15, 2004

(65) Prior Publication Data

US 2006/0093640 A1    May 4, 2006

(30) Foreign Application Priority Data

Jun. 20, 2002    (ZA)    .................................. 2002/4977

(51) Int. Cl.
| | |
|---|---|
| C07K 14/435 | (2006.01) |
| C07K 14/46 | (2006.01) |
| C07K 14/47 | (2006.01) |
| C07K 14/475 | (2006.01) |
| C07K 14/51 | (2006.01) |
| C07K 1/00 | (2006.01) |
| C07K 1/14 | (2006.01) |
| C07K 1/16 | (2006.01) |
| C07K 1/22 | (2006.01) |
| C07K 1/34 | (2006.01) |
| C07K 1/36 | (2006.01) |

(52) U.S. Cl. ........................ 530/412; 530/413; 530/414; 530/417; 530/422; 530/427; 530/350

(58) Field of Classification Search ........................ None
See application file for complete search history.

(56) References Cited

U.S. PATENT DOCUMENTS

| | | | |
|---|---|---|---|
| 4,968,590 A | * | 11/1990 | Kuberasampath et al. ... 530/326 |
| 5,371,191 A | | 12/1994 | Poser et al. |
| 6,030,635 A | | 2/2000 | Gertzman et al. |

FOREIGN PATENT DOCUMENTS

| | | |
|---|---|---|
| EP | 0148155 A2 | 2/1985 |
| EP | 0474174 A2 | 3/1991 |
| WO | WO 96/39203 | 12/1996 |
| WO | WO 98/040113 | 9/1998 |
| WO | WO 99/38543 | 8/1999 |

OTHER PUBLICATIONS

Ugo Ripamonti,, M.D., et al., Reconstruction of the Bone-Bone Marrow Organ by Osteogenin, a Bone Morphogenetic Protein, and Demineralized Bone Matrix in Calvarial Defects of Adult Primates, Plastic and Reconstructive Surgery, 27-36, (Jan. 1993).

Caroline Kelly Scott, et al., Intramembranous Bone Matrix is Osteoinductive, The Anatomical Record, 238:23-30 (1994).

Shelley R. Winn, Ph.D., et al., Carrier Systems for Bone Morphogenetic Proteins, Clinical Orthopaedics and Related Research, No. 367S, pp. S95-S106, (1999).

Yoshiyuki Yoshimura, et al., Purification of Water-Soluble Bone-Inductive Protein from Bovine Demineralized Bone Matrix, Biol. Pharm. Bull. 16(5) 444-447, (1993).

M.R. Urist, et al., Purification of bovine bone morphogenetic protein by hydroxyapatite chromatography, Proc. Natl. Acad. Sci. USA, vol. 81, pp. 371-375, (Jan. 1984).

* cited by examiner

*Primary Examiner*—Elizabeth C. Kemmerer
(74) *Attorney, Agent, or Firm*—The Webb Law Firm

(57) ABSTRACT

In a method of isolating osteogenic protein from bone, in which an osteogenic protein-containing fraction is extracted from bone and enriched by a sequence of enrichment steps selected from ultrafiltration and chromatography, the invention provides the improvement of removing higher molecular weight components from the osteogenic protein-containing fraction prior to the enrichment steps. The higher molecular weight components have a molecular weight of about 100-300 kDa and are selected from collagen, collagen fragments, collagen aggregates and mixtures thereof.

1 Claim, 2 Drawing Sheets

FIGURE 2. Non-union in a patient after attempts to treat defect conventionally had failed.
FIGURE 3. Same patient treated with the composite hBMP material and internal nail. Complete healing and visible new bone evidenced at 16 weeks post operatively.

METHOD OF PREPARING AN OSTEOGENIC PROTEIN FRACTION

BACKGROUND OF THE INVENTION

1. Field of the Invention

THIS INVENTION relates to osteoinductive biomaterials. In particular the invention relates to an osteogenic composition and to the use of an osteogenic composition in therapy.

2. Description of Related Art

The osteogenic composition of the invention is particularly intended for human or mammalian tissue regeneration and for promoting or inducing bone growth. For the purposes of this specification, the phrase "osteogenic protein" refers to the material which is obtained by fractionation of total mammalian bone protein and which is capable of inducing bone formation. The terms "osteogenic" and "osteoinductive" are considered to be synonymous. Osteogenesis is the term used to describe the de novo formation of bone in adult mammals and is evidenced in adults during regeneration of bone fractures. It proceeds via a process which closely resembles embryonic osteogenesis. Osteogenic protein contains, amongst other unidentified proteins, Bone Morphogenetic Proteins (BMPs). This is a family of characterized proteins which have been classified as part of the larger transforming growth factor-beta superfamily of morphogenic proteins. The BMP family comprises more than a dozen individual members which are known to be capable of inducing bone formation in mammals.

Mammalian bone tissue is host to a family of protein growth and differentiation factors, called the bone morphogenetic proteins (BMPs). These proteins are capable of inducing new bone formation when implanted in adolescent and adult mammals.

The BMPs are redeployed in adults to cause regeneration of bone via mechanisms closely resembling embryonic differentiation. The developmental cascade of bone differentiation consists of chemotaxis of mesenchymal cells, proliferation of progenitor cells, differentiation of cartilage, vascular invasion, bone formation, remodeling, and finally marrow differentiation (Reddi, (1981) Collagen Rel. Res. 1:209-226). It has been shown that the natural endochondral bone differentiation activity of bone matrix can be dissociatively extracted and reconstituted with inactive residual matrix to restore full bone inductive activity (Sampath and Reddi, (1981) Proc. Natl. Acad. Sci. USA 78:7599-7603). The purification of osteogenin, an osteogenic protein from mammalian bone is disclosed by Sampath et al. (1987) (Proc. Natl. Acad. Sci. USA 84, 7109-7113). Urist et al. (Proc. Natl. Acad. Sci. USA (1984) 81:371-375) disclose a bovine bone morphogenetic protein extract having the properties of an acidic polypeptide and a molecular weight of approximately 18 kD. The authors report that the protein is present in a fraction separated by hydroxyapatite chromatography, and that it induces bone formation in mouse hindquarter muscle and bone regeneration in trephone defects in rat and dog skulls.

European Patent Application No. 148,155, published Oct. 7, 1985, discloses osteogenic proteins derived from bovine, porcine, and human origin. One of the proteins, designated by the inventors as a P3 protein and having a molecular weight of 22-24 kD, is reported to have been purified to an essentially homogeneous state. This material is reported to induce bone formation when implanted into animals.

SUMMARY OF THE INVENTION

According to a first aspect of the invention, in a method of isolating osteogenic protein from bone, in which an osteogenic protein containing fraction is extracted from bone and enriched by a sequence of enrichment steps selected from ultrafiltration and chromatography, there is provided the improvement of removing higher molecular weight components from the osteogenic protein containing fraction prior to the enrichment steps.

The higher molecular weight components may have a molecular weight of about 100-300 kDa. The higher molecular weight components will typically include collagen, collagen fragments, collagen aggregates and mixtures thereof.

The method may include removing the higher molecular weight components by ultrafiltration. For example, the components may be removed by ultrafiltration through a 100-300 kDa nominal molecular weight membrane such as a 100-300 kDa nominal molecular weight polysulphone membrane.

The osteogenic protein containing fraction may be extracted from the bone using a chaotropic solution. The chaotropic solution may contain urea, guanidinium chloride or combinations thereof.

The enrichment steps may include successive ultra-filtration of the osteogenic protein containing fraction through progressively smaller nominal molecular weight membranes followed by, or interspersed with, chromatographic enrichment steps. The enrichment steps may thus include one or more chromatographic enrichment steps.

The osteogenic protein containing fraction may be concentrated and desalted through successive ultra-filtration steps. The fraction may be concentrated and desalted through 10 kDA and 5 kDA ultra-filtration steps.

The chromatographic enrichment steps may be selected from one or more of heparin-sepharose chromatography, hydroxyapatite chromatography, reverse-phase silica chromatography and combinations of any two or more thereof.

According to a second aspect of the invention, there is provided a bone growth inducing composition which includes osteogenic protein, insoluble bone matrix (ICBM) and gelatin.

The composition may be in the form of a hydratable powder.

The insoluble bone matrix may be prepared by demineralizing whole bone powder with acid to produce an acid demineralised whole bone powder or matrix, extracting soluble components from the demineralised bone powder or matrix with a chaotropic agent such as aqueous urea or a guanidinium solution, water-washing the residue and then drying the residue to produce insoluble bone matrix.

The gelatin may be obtained by extracting insoluble bone matrix to produce a fraction rich in soluble collagen type I, precipitating the soluble collagen type I and drying the precipitate in vacuo.

The extraction may be with purified boiling water and the precipitation may be with ethanol.

The insoluble collagenous bone matrix may be mammalian. It may be non-human or human insoluble collagenous bone matrix. It is preferably human insoluble collagenous bone matrix or hICBM. The gelatin may accordingly be human gelatin.

The osteogenic protein may be prepared by a method as hereinbefore described.

The mass ratio between the osteogenic protein, the hICBM and the human gelatin may be about 0.4-0.6: 800-1200: 100-1000.

Thus, the bone growth inducing composition may include the osteogenic protein in an amount of about 400-600 μg, the hICBM in an amount of about 800-1200 mg and the human gelatin in an amount of about 100-1000 mg. In a preferred embodiment, the bone growth inducing composition includes the osteogenic protein in an amount of about 500 μg, the hICBM in an amount of about 1000 mg and the human gelatin in an amount of about 200 mg.

The invention extends to a bone growth inducing composition as described above in which the osteogenic protein is prepared by an improved method as described above.

According to another aspect of the invention, there is provided a method of preparing a bone growth inducing composition, the method including the steps of combining osteogenic protein, insoluble bone matrix and gelatin.

The insoluble collagenous bone matrix may be mammalian and may be selected from non-human and human insoluble collagenous bone matrix. It is preferably human insoluble collagenous bone matrix or hICBM. The gelatin may be human gelatin.

The osteogenic protein may be prepared by a method as hereinbefore described.

The osteogenic protein, the hICBM and the human gelatin may be combined in a mass ratio of 0.4-0.6: 800:1200: 100-1000.

The method may thus include combining the osteogenic protein in an amount of about 400-600 μg, the hICBM in an amount of about 800-1200 mg and the human gelatin in an amount of about 100-1000 mg. In a preferred embodiment, the method may include combining the osteogenic protein in an amount of about 500 μg, the hICBM in an amount of about 1000 mg and the human gelatin in an amount of about 200 mg.

The method may include combining the osteogenic protein with the hICBM in a dilute aqueous acidic solution, lyophilising the resulting mixture to produce a dry powder and mixing the powder with the human gelatin to produce a hydratable material.

According to another aspect of the invention, there is provided a device for inducing bone growth in a mammal, the device including a bone growth inducing composition which comprises osteogenic protein, insoluble bone matrix and gelatin and a delivery mechanism for delivery of the composition to a treatment site.

The osteogenic protein, the insoluble bone matrix and the gelatin may be as hereinbefore described. The delivery mechanism may be a syringe.

In particular, the composition may be the hydratable powder hereinbefore described which may be contained in the syringe. Thus, by drawing an aqueous saline solution up into the syringe, the material may be hydrated for injection into the delivery site.

According to another aspect of the invention, there is provided a method of inducing bone formation in a mammal having a skeletal defect, the method including the step of implanting a bone inducing composition as hereinbefore described into the skeletal defect of the mammal.

According to another aspect of the invention, there is provided a method of inducing the growth of ectopic bone in a mammal, the method including the step of implanting a bone inducing composition as hereinbefore described in a non-bony site of the mammal.

According to another aspect of the invention, there is provided a method of accelerating allogeneic bone healing in a mammal, the method including the step of implanting allogeneic bone material together with a bone inducing composition as hereinbefore described into site in which allogeneic bone healing in the mammal is required.

The allogeneic bone material may be tissue-banked bone including human cortical bone chips, cancellous bone blocks, cancellous bone powder, whole bone or demineralised bone matrix.

According to another aspect of the invention, there is provided a method of accelerating autogenous bone graft healing in a mammal, the method including the step of implanting autogenous bone material together with a bone inducing composition as hereinbefore described into site in which autogenous bone graft healing in the mammal is required.

The autogenous bone material may be iliac crest autogenous bone.

According to another aspect of the invention, there is provided a substance or composition for use in a method of inducing bone formation in a mammal having a skeletal defect, the substance or composition comprising a bone growth inducing composition as hereinbefore described and the method including implanting the composition into a skeletal defect of the mammal.

According to another aspect of the invention, there is provided a substance or composition for use in a method of inducing the growth of ectopic bone in a mammal, the substance or composition comprising a bone growth inducing composition as hereinbefore described and the method including the step of implanting the composition in a non-bony site of the mammal.

According to another aspect of the invention, there is provided a substance or composition for accelerating allogeneic bone healing in a mammal, the substance or composition comprising a bone growth inducing composition as hereinbefore described and the method including the step of implanting allogeneic bone material together with the composition into a site in which allogeneic bone healing in the mammal is required.

The allogeneic bone material may be tissue-banked bone selected from human cortical bone chips, cancellous bone blocks, cancellous bone powder, whole morselised bone or demineralised bone matrix.

According to another aspect of the invention, there is provided a substance or composition for accelerating autogenous bone graft healing in a mammal, the substance or composition comprising a bone growth inducing composition as hereinbefore described and the method including the step of implanting autogenous bone material together with the composition into a site in which autogenous bone graft healing in the mammal is required.

The autogenous bone material may be morselised iliac crest autogenous bone.

According to another aspect of the invention, there is provided the use of a substance or composition in the preparation of a medicament for use in a method of inducing bone formation in a mammal having a skeletal defect, the substance or composition comprising a bone growth inducing composition as hereinbefore described.

According to another aspect of the invention, there is provided the use of a substance or composition for the preparation of a medicament for use in a method of inducing the growth of ectopic bone in a mammal, the substance or composition comprising a bone growth inducing composition as hereinbefore described.

According to another aspect of the invention, there is provided the use of a substance or composition in the preparation of a medicament for accelerating allogeneic bone healing in a mammal, the substance or composition comprising a bone growth inducing composition as hereinbefore described and an allogeneic bone material.

The allogeneic bone material may be tissue-banked bone selected from human cortical bone chips, cancellous bone blocks, cancellous bone powder, whole bone or demineralised bone matrix.

According to another aspect of the invention, there is provided the use of a substance or composition in the preparation of a medicament for accelerating autogenous bone graft healing in a mammal, the substance or composition comprising a bone growth inducing composition as hereinbefore described and an autogenous bone material.

The autogenous bone material may be morselised iliac crest autogenous bone.

This invention accordingly relates to the preparation of osteogenic protein from mammalian bone and to its use in conjunction with a matrix in bone repair.

DETAILED DESCRIPTION OF THE INVENTION

It is an object of the invention to provide a method for the preparation of osteogenic protein from mammalian bone tissue in high yield. Another object is to provide bone-inducing devices comprising osteogenic protein adsorbed onto matrix as a delivery system for said bone morphogenetic proteins.

The invention provides osteogenic devices which, when implanted at a skeletal defect site of the mammal, induce at the site of implantation the full regeneration of bone and the consequent healing of the defect. The device comprises a matrix carrier material, as described below, and osteogenic protein, a fraction of total extractable bone protein which contains bone morphogenetic proteins (BMPs).

Osteogenic protein requires the presence of a suitable delivery material to exert its bone regenerating effects. Matrix purified from demineralised bone matrix is such a suitable material and is described in more detail below.

The method used to isolate osteogenic protein exploits in part, the published procedure of Sampath et al. (1987) (Proc. Natl. Acad. Sci. USA 84, 7109-7113. This procedure exploits the BMPs' affinity for heparin and hydroxyapatite immobilized onto chromatographic support matrices to achieve isolation of BMP rich fractions. The procedure entails the chromatography of urea extracts of demineralised bone onto a heparin chromatography column, followed by a hydroxyapatite column, and finally gel exclusion chromatography to eliminate heavy molecular weight contaminants. Although this procedure results in the effective isolation of a fraction with osteogenic capacity, the quantity, yield and speed of purification of osteogenic protein using the method of the present invention is greatly improved.

The preparation of the osteogenic protein of the invention is based on the procedure of Sampath et al (1987), but includes a novel and inventive modification.

The key modification involves the fractionation of the total bone protein extract into a high and a low molecular weight fraction at the beginning of the purification process, before chromatography. The bone morphogenetic proteins have a molecular weight of approximately 30 kDa and, for the purposes of this specification, are classed as low molecular weight polypeptides. For the purposes of this specification, high molecular weight polypeptides include polypeptides with a molecular weight greater that 100 kDa and especially greater that 300 kDa. The high molecular weight fraction will include collagen and collagen fragments (approximately 100 kDa) as well as collagen aggregates (200 kDa and greater) and other unidentified polypeptides, some of which are thought to be inhibitors of morphogen-induced osteogenesis. It is important to note, for the purposes of this specification, that collagens are separated from the low molecular weight fraction at the beginning of the process before the heparin affinity chromatography step.

The removal of collagen is important for the following reasons. Firstly, collagen type I is known to have an affinity for BMPs (Reddi AH (1995) Cartilage morphogenesis: role of bone and cartilage morphogenetic proteins, homeobox genes and extracellular matrix. Matrix Biol. October 14(8): 599-606.; Winn S R, Uludag H, Hollinger J O. (1999) Carrier systems for bone morphogenetic proteins. Clin Orthop 1999 October (367 Suppl):S95-106). Secondly, peptides are large MW peptides which tend to foul columns and alter the exchange dynamics of the BMP with the binding sites on the heparin molecule in a way which hampers binding. Furthermore, it appears that there may exist inhibitors of bone morphogenetic proteins, the active constituent of osteogenic protein, that reside in the high molecular weight fraction of total extractable bone protein. This implies that there exists competitive binding for BMPs between collagen type I and heparin. This competitive binding interference appears to result in yield losses during the chromatographic purification of BMPs on a heparin column. The method of this invention results in a significant improvement in the recovery of total osteogenic activity over prior art methods.

The invention is now described, by way of example with reference to the following Examples.

BRIEF DESCRIPTION OF THE DRAWINGS

FIG. 2 shows non-union in a bone of a patient after conventional treatment; and

FIG. 3 shows complete healing of the bone of the patient of FIG. 2 after treatment in accordance with the method of the invention

EXAMPLE 1

Figure 1:
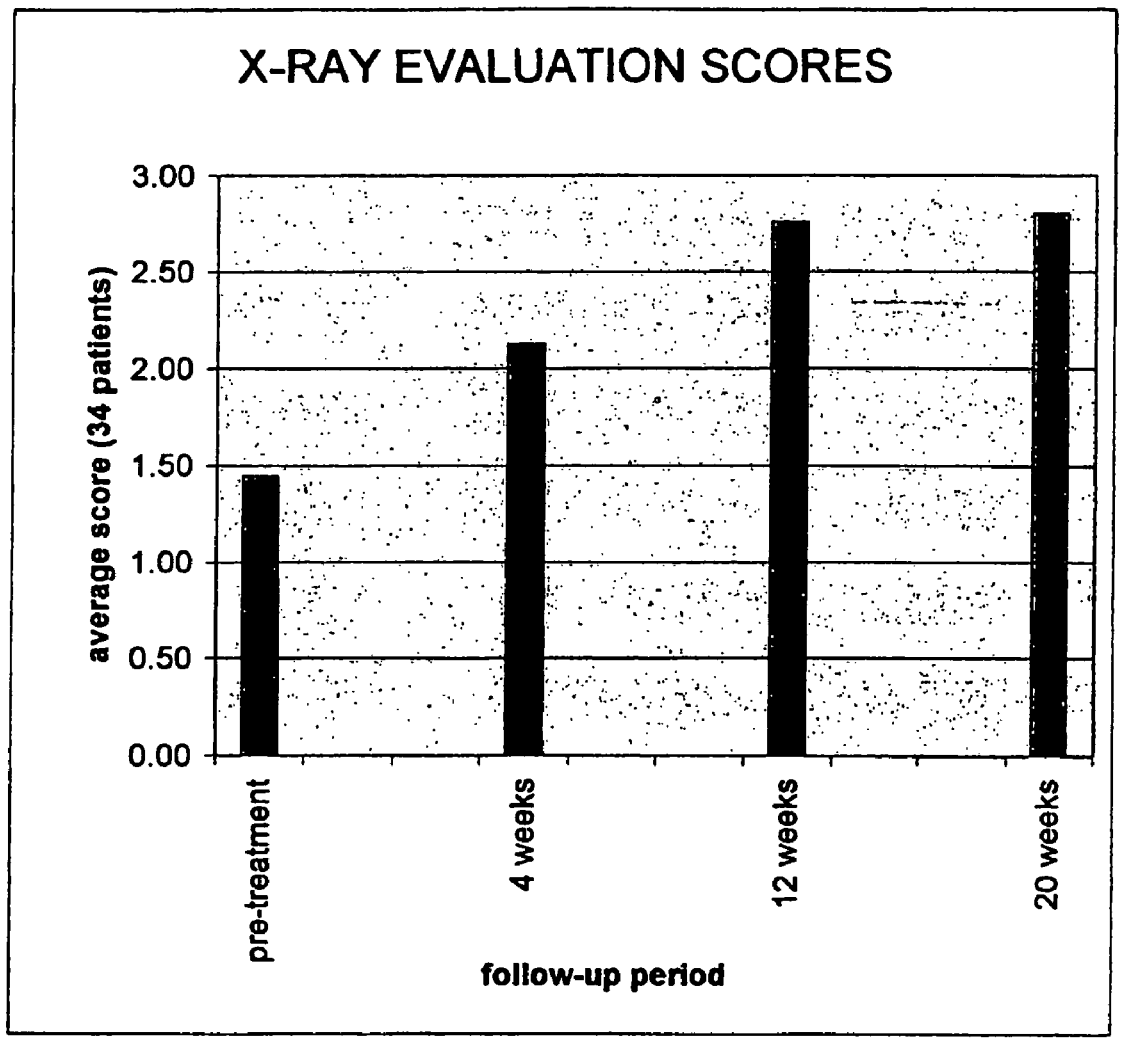
FIG. 1 shows X-ray evaluation scores of treated non-unions as a function of time.

Purification of Human Osteogenic Protein Containing Bone Morphogenetic Proteins

1. Preparation of Demineralised Bone

Human long bone diaphyses, freed from adhering soft tissues, were demarrowed and cut into pieces of between 1 and 4 cm. Batches of this material were defatted in a solvent system comprising a 50:50 ratio by volume of methanol and chloroform, at 4° C.-8° C. for 16-24 hours. The bone was then dehydrated in absolute alcohol for 48 hours at 4° C.-8° C. The alcohol was decanted and the bone was air-dried in a fume hood for 48-96 hours. The bone was then milled in a hammer mill to a particle size ranging from 10 to 425 micron.

The particulate material was demineralised at room temperature, with consecutive additions of four to five volumes of 0.5 M HCl, until acid base reaction between the hydroxyapatite of the bone and the HCl had neared completion as judged by slowing pH changes over time. The demineralised bone was neutralized with dilute sodium bicarbonate solution, and washed with purified water to produce demineralised bone matrix.

2. Dissociative Extraction of Demineralised Bone Matrix

Demineralised bone matrix (DBM) from the previous step was extracted twice with three to four volumes of 8M urea, 50 mM Tris-HCl, pH 7.4, containing protease inhibitors (5 mM benzamidine hydrochloride, 0.1 M 6-aminohexanoic acid, 5 mM N-ethylmaleimide and 0.5 mM phenylmethylsulfonyfluoride) for 24 hours at 4° C. to 8° C. The supernatant was collected by filtration through a porous polypropylene frit, and filtered through a three micron nominal size cartridge filter (Polygard, Millipore Corporation, USA).

3. Ultrafiltration Fractionation of High Molecular Weight Components

Heavy molecular proteins and collagens were removed by ultrafiltration of the supernatant from the step 2 through a polysulfone 300 kDa nominal molecular weight membrane (Millipore, Cat. No. CDUF006TM). A 100 kDa nominal molecular weight membrane can optionally be employed with somewhat lower yields of total BMP activity, but with higher specific activity. This procedure removed collagens, especially type I collagens, which bind BMPs under conditions of lower ionic strength. The retentate was washed a few times with 6 M urea buffer, 50 mM Tris-HCL pH 7.4 (Buffer A), and the diafiltrate which contained the osteogenic activity was collected.

4. Concentration and Desalting by Ultrafiltration Buffer Exchange

The diafiltrate containing the osteogenic proteins (molecular weight circa 30 kDa) from step 3 was desalted and concentrated by ultrafiltration on a 10 kDa PLGC membrane (Millipore, Cat. No. SK1P003W4). This step effectively removed salt and other low MW weight components, to create the required conditions for the following chromatographic step. Successive volumes of Buffer A containing the aforementioned concentrations of enzyme inhibitors but excluding n-ethyl maleimide were added to the retentate following concentration, until the conductivity of the retentate reached between 5.0 and 6.0 milli Siemens.

5. Heparin-Sepharose Chromatography

The retentate from step 4 was chromatographed onto Heparin-Sephahrose CL-6b (Pharmacia-Amersham) which had been equilibrated with buffer A containing 0.15 M NaCl. The column was washed with three column volumes of buffer A containing 0.15 NaCl and then eluted with buffer A containing 0.5 M NaCl. The eluting peak with absorbance at 280 nm was collected and stored at 4° C.

6. Ultrafiltration Exchange of Heparin-Sepharose Affinity Fraction

The Heparin-Sepharose affinity fraction from step 5 was desalted and concentrated by ultrafiltration on a PLCC 5 kDa membrane (Millipore, Cat. No. CDUF001LC). This step effectively removed salt and other low MW weight components, to create the required conditions for the next chromatographic step. Successive volumes of Buffer A containing 10 mM sodium phosphate were added to the retentate following concentration, until the conductivity of the retentate had reached between 5.0 and 6.0 milli Siemens.

7. Hydroxyapatite (HA) Chromatography

The retentate from step 6 was chromatographed onto a hydroxyapatite column (Hydroxyapatite Ultrogel, Biosepra, France) which had been equilibrated in Buffer A containing 10 mM sodium phosphate. The column was washed with three column volumes of Buffer A containing 10 mM sodium phosphate. An osteogenic protein enriched fraction was eluted with Buffer A containing 150 mM sodium phosphate. The eluting peak with absorbance at 280 nm was collected and stored at 4° C.

8. Exchange of HA Affinity Fraction into 10 mM HCl

The HA affinity fraction from step 7 was exchanged into a 10 mM HCl solution using an Amicon stirred Ultrafiltration cell (Millipore Corporation, U.S.A.) loaded with a 3 kDa cutoff cellulose membrane (YM3, 76 mm regenerated cellulose, Millipore Corporation U.S.A.).

In an embodiment of the invention, the HA affinity fraction was instead loaded onto a C-18 Vydac silica-based HPLC column (particle size 5 um, pore size 300 A). The column was washed with 0.1% trifluoroacetic acid, 10% acetonitrile for 10 column volumes, and the bound proteins were step eluted with a 70% acetonitrile, 0.1% trifluoroacetic acid. This material was lyophilized and reconstituted into 10 mM HCl.

The process flow chart with protein values is set out in Table 1.

TABLE 1

| Step | Procedure | Total protein (mg) |
|---|---|---|
| 1 | Dehydrated, defatted human bone powder 5 kg. | Not determined |
| 2 | Extraction with chaotropic solution containing urea or guanidinium chloride | 17 703 |
| 3 | Filtration through a Millipore Polygard CR cartridge filter with a 3.0 micron nominal pore size product no. CR0301006. | Not determined |
| 4 | Ultrafiltration employing a membrane with a nominal pore size of 300 kD | 15 069 |
| 5 | Ultrafiltration and buffer exchange employing a membrane with a nominal pore size of 10 kD | 8 881 |
| 6 | Heparin affinity fraction | 211.43 |
| 7 | Hydroxyapatite affinity fraction | 62.99 |
| 8 | Ultrafiltration exchange or HPLC | 40–60 |

500 µg of the material from step 8 of Example 1, delivered on 1.2 grams of matrix, induces new bone formation in recalcitrant long-bone non-unions in humans. The material from step 8 was analysed by S-200 gel filtration chromatography (Pharmacia) and found to contain 20% by mass of high molecular weight components. These may be optionally removed by a 'polishing' step employing gel exclusion chromatography on S-200 matrix (Pharmacia) and elution with 8M Urea, 1 M NaCl, 50 mM Tris-HCl pH 7.4. The final yield is in the region of 30 mg to 50 mg of osteogenic protein. These yields are approximately four-fold higher than those previously reported for baboon bone extraction employing a comparative starting bone material and method on hydoxyapatite affinity, heparin affinity and gel exclusion chromatography on S-200 matrices (Pharmacia)(Ripamonti U, Ma S S, Cunningham N S, Yeates L, Reddi A H (1993) Reconstruction of the bone-bone marrow organ by osteogenin, a bone morphogenetic protein, and demineralised bone matrix in calvarial defects of adult primates (Plastic and Reconstructive Surgery 91(1):27-36). Comparative histomorphometric studies between iliac crest bone biopsies of humans and baboons have demonstrated a remarkable degree of similarity between the two species (Schnitzler C M, Ripamonti U, and Mesquita J M (1993) Histomorphometry of iliac crest trabecular bone in adult male baboons in captivity, Calcif. Tiss. Int., 52, 447-454).

EXAMPLE 2

Determination of Osteogenic Activity of Osteogenic Protein

Bioassay in Rats

Osteogenic activity was bioassayed as described by Sampath and Reddi (Proc. Natl. Acad. Sci. USA (1983) 80:6591-

6595). The assay consists of implanting test samples comprising insoluble bone matrix and human osteogenic protein in subcutaneous sites in recipient rats under ether anesthesia. A vertical incision (1 cm) was made under sterile conditions in the skin over the thoracic region, and bilateral pockets were prepared by blunt dissection. Implants comprised 25 mg rat ICBM, 50 mg rat tail type I collagen in 0.5 M acetic acid, and osteogenic protein in varying amounts. The test sample was implanted bilaterally into each pocket and the incision was closed with stitches. The heterotropic site allowed for the study of bone induction without the possible ambiguities resulting from the use of bony sites.

Regenerated tissues were explanted on day 12 post-implantation and assayed for alkaline phosphatase activity, a marker for bone formation, as described (Reddi and Sullivan 1980 Endocrinology 107:1291-1299). Results and data are presented in Table 2.

TABLE 2

| | |
|---|---|
| Rat bioassay replicates | 4 |
| Micrograms osteogenic protein assayed per implant | 100 μg |
| Alkaline phosphatase activity units/mg protein (average 4 replicates) | 8.82 U/mg (sd = 3.8) |

*hICBM—human insoluble bone matrix.

The implant model in rats exhibited a controlled progression through the stages of osteogenic protein induced endochondral bone development. This postfoetal osteogenesis may be considered to recapitulate events that occur in the normal course of embryonic bone development. The new bone resulted from local mesenchymal condensations, a cartilage phase and extracellular matrix production, vascular invasion and mineralisation, and finally the formation of new bone via the differentiation of osteoprogenitor cell lines.

Histological analysis employing staining with toluidine blue or hemotoxylin/eosin demonstrated clearly the development of endochondrial bone. Twelve day implants were usually sufficient to determine whether the implants showed bone inducing activity.

Alkaline phosphatase activity may be used as a marker for osteogenesis. The enzyme activity may be determined spectrophotometrically after homogenization of the implant and assaying of enyme activity with the substrate p-nitrophenyl phosphate under alkaline conditions. Implants showing no bone development by histology should have no alkaline phosphatase activity under these assay conditions (Reddi A H and Sullivan N E (1980) Endocrinology 107, 1291-1299). The assay is useful for quantitation of the specific and total activity of alkaline phosphatase, which may then be correlated to the osteoinductive potency of the prepared osteogenic protein described herein.

Alkaline phosphatase activity is calculated according to the method of Reddi and Sullivan (1980, Endocrinology 107, 1291-1299). Induction of 1 unit or more of alkaline phosphatase by a rat implant indicates effective osteogenesis.

EXAMPLE 3

Preparation of Human Gelatin

An amount of ICBM was combined with five to ten volumes of water in a borosilicate glass bottle and heated in a pressure cooker for one hour. The supernatant was filtered through Whatman no. 1 paper or a 20 micron stainless steel mesh. The gelatinous solution was cooled to 25° C. and 5 volumes of chilled ethanol (−20° C.) were added to precipitate collagen. The precipitate was dried in vacuo, and milled to a size range of 75 to 425 micron.

EXAMPLE 4

Fabrication of Osteogenic Devices

Human ICBM was used as the adsorptive carrier matrix for the fabrication of the osteoinductive composite biomaterial. Inactive ICBM was restored to biological activity when a sufficient amount of osteogenic protein was combined with ICBM. The particle size of the ICBM influences the quantitative response of new bone. Particles between 75 and 420 μm elicit the maximum response. An amount of ICBM was combined with osteogenic protein in 10 mM HCl and thoroughly mixed with sterile spatula. The material was lyophilized to dryness.

This material was then combined with human ICBM-derived gelatin. The components were thoroughly dry-mixed together to obtain a homogeneously distributed composition. The human gelatin acted as a readily hydratable material that causes the biomaterial to become extrudable. The composite was packed into a syringe. The osteoinductive composite was rehydrated at the time of use. Rehydration was achieved when an amount of sterile saline or water was drawn into the syringe, and approximately 10 minutes allowed for rehydration to occur. The material could then easily be expelled out of the syringe by depressing the plunger. This allowed for precise implant deposition into a defect site at the time of surgery. The implant may be further contained in situ using standard gelatinous sponges such as Spongostan (Johnson and Johnson Medical Limited, U.K.).

The carrier could be replaced by either a biodegradable-synthetic or synthetic-inorganic matrix (e.g., HAP, collagen, tricalcium phosphate, or polylactic acid, polyglycolic acid and various copolymers thereof).

Table 3 sets out a typical formulation for the osteogenic composition.

TABLE 3

| Material | Amount |
|---|---|
| Osteogenic protein | 500 μg |
| hICBM* | 1000 mg |
| Human gelatin | 200 mg |
| TOTAL | 1200 mg |

*hICBM—human insoluble bone matrix.

EXAMPLE 5

Testing of Osteogenic Composition in Humans

Implants containing 500 micrograms of human osteogenic protein adsorbed onto a composite matrix comprising 1 g of insoluble bone matrix and 200 mg of lyophilized human gelatin were prepared. Thirty-four patients with resistant nonunions including partial or complete segmental defects were treated with the osteogenic composite. The series consisted of 11 females and 23 males. The average age was 36 years. All patients had previously been variously treated by internal or external fixation, cast, and/or autogeneic bone grafting, and failed to achieve union. Preoperative symptoms averaged 26 months (range, one to 228 months). The implant was incorporated at the time of surgery by injecting the hydrated implant at the defect site, which was further stabilised by internal or external fixation. An average of 2.4 g of the composite was used per patient. Seventeen patients additionally received supplementary bone which included cancellous bone particles and block configured spongy bone. Functional results were rated according to weight-bearing function at follow-up periods of 1, 8, 16 and 24 week periods postoperatively. A zero score was allocated where there was no weight bearing, a one score allocated for weight bearing with the assistance of two crutches, a two score allocated for light weight bearing with one crutch, a three score allocated for full weight bearing with one crutch and a four score allocated for full weight bearing with no crutch assistance. The average score was 3.25 for an average follow-up time of 17 weeks (range eight to 32 weeks). This score was higher than the pre-operative score of 2.22 and the post-operative score (week 1) of 0.5. Of the five patients who suffered recurrent infection, two failed to score above 2 at 18.5 weeks average follow-up period. Bridging was as assessed radiographically by trained clinicians according to a scale from 1 to 5 where 1=non-union/no callus, 2=callus present without bridging, 3=moderate bridging, 4=good bridging, 5=complete union. The average score for the treatment group on follow-up period of 20 weeks was 2.80 in comparison to the pre-treatment score of 1.44. The results indicate that the osteogenic composite implant of the invention results in effective treatment of difficult nonunions. The scores as measured at different follow-up periods are presented in FIG. 1.

It is an advantage of the invention that the multistep developmental cascade of bone induced by the osteogenic biomaterial composite of the invention includes binding of fibrin and fibronectin to the biomaterial, chemotaxis of cells, proliferation of fibroblasts, mesenchymal condensation, differentiation into chondroblasts, chondrogenesis, vascular invasion, bone formation, remodeling, and bone marrow differentiation.

The injectable biomaterial of the invention offers several advantages. It may be stored at room temperature for lengthy periods without marked deterioration in biological activity. It may be readily rehydrated at the time of surgery and it is easily handled, merely requiring the depression of the syringe plunger to expel the osteogenic material as required.

From a clinical context, the osteogenic biomaterial composite offers the following advantages. It is osteogenic, inducing bone at the site of implantation. It obviates the need to perform a second operation at the patient's hip to harvest autologous bone and it obviates the need to use tissue banked bone. This reduces the risk of transmissible diseases.

The ICBM binds osteogenic protein and acts as a slow release delivery system to activate progenitor cells at the site of implantation. The composite biomaterial of the invention accommodates each step of the cellular response during bone development. It is biocompatible, and is resorbed during osteogenesis and replaced by the host's own bone.

The geometry of the described biomaterial as measured by its particle size, is optimal in permitting cell infiltration and differentiation.

The invention claimed is:

1. A method of preparing an osteogenic protein fraction, comprising:

extracting demineralized bone matrix with a solution of at least one chaotropic agent selected from the group consisting of urea and guanidinium salts to produce an extract;

removing high molecular weight proteins which exceed 300 kDA from the extract by ultrafiltration with a 300 kDA membrane to produce a lower molecular weight fraction;

subjecting the lower molecular weight fraction to heparin affinity chromatography under conditions which first favor the binding and then the elution of a purified heparin affinity fraction containing the osteogenic protein fraction;

subjecting the heparin affinity fraction to hydroxyapatite chromatography under conditions which first favor the binding and then the elution of a purified osteogenic protein fraction; and exchanging the purified osteogenic protein fraction into a solvent suitable for human medical use.

\* \* \* \* \*